United States Patent

Novak et al.

(10) Patent No.: US 8,343,178 B2
(45) Date of Patent: Jan. 1, 2013

(54) METHOD FOR ULTRASONIC TISSUE EXCISION WITH TISSUE SELECTIVITY

(75) Inventors: Theodore A. D. Novak, King Park, NY (US); Werner Sladek-Maharg, Coram, NY (US); Dan Voic, Clifton, NJ (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 2340 days.

(21) Appl. No.: 11/196,607

(22) Filed: Aug. 2, 2005

(65) Prior Publication Data

US 2005/0273127 A1     Dec. 8, 2005

Related U.S. Application Data

(62) Division of application No. 10/137,470, filed on Apr. 30, 2002, now abandoned.

(51) Int. Cl.
*A61B 17/32* (2006.01)

(52) U.S. Cl. ........................................................ 606/169

(58) Field of Classification Search ................ 606/79, 606/169
See application file for complete search history.

(56) References Cited

U.S. PATENT DOCUMENTS

| | | |
|---|---|---|
| 878,524 A | 2/1908 | Gregory |
| 1,333,745 A | 3/1920 | Wescott |
| 2,845,072 A | 7/1958 | Shafer |
| 3,526,219 A | 9/1970 | Balamuth |
| 3,636,943 A | 1/1972 | Balamuth |
| 3,832,776 A | 9/1974 | Sawyer |
| 4,008,720 A | 2/1977 | Brinckmann et al. |
| 4,667,408 A | 5/1987 | Kirk |
| 4,832,683 A | 5/1989 | Idemoto et al. |
| 5,188,102 A * | 2/1993 | Idemoto et al. ............. 604/22 |
| 5,261,922 A | 11/1993 | Hood |
| 5,322,055 A | 6/1994 | Davison et al. |
| 5,391,144 A | 2/1995 | Sakurai et al. |
| 5,674,235 A | 10/1997 | Parisi |
| 6,254,622 B1 | 7/2001 | Hood |
| 2001/0004695 A1 * | 6/2001 | Vercellotti et al. ............. 606/79 |
| 2002/0103497 A1 * | 8/2002 | Satou ........................ 606/169 |

* cited by examiner

*Primary Examiner* — Ryan Severson
(74) *Attorney, Agent, or Firm* — R. Neil Sudol; Coleman Sudol Sapone P.C.

(57) ABSTRACT

A surgical method utilizes a cutting blade having a thickness along a cutting edge of between about 0.0005 inch and about 0.020 inch and preferably between about 0.001 inch and 0.010 inch. The blade is moved in contact with relatively hardly tissues which are disposed adjacent to softer tissues at a surgical site in a patient. The blade is ultrasonically vibrated during the moving of the blade, whereby the hard tissue is cut with a modicum of damage being inflicted on the soft tissue.

10 Claims, 1 Drawing Sheet

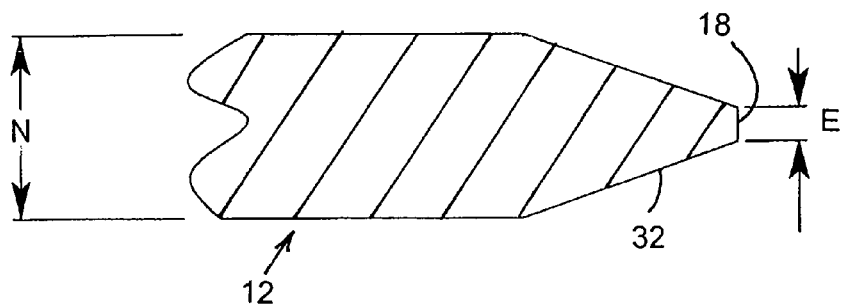
FIGURE 1
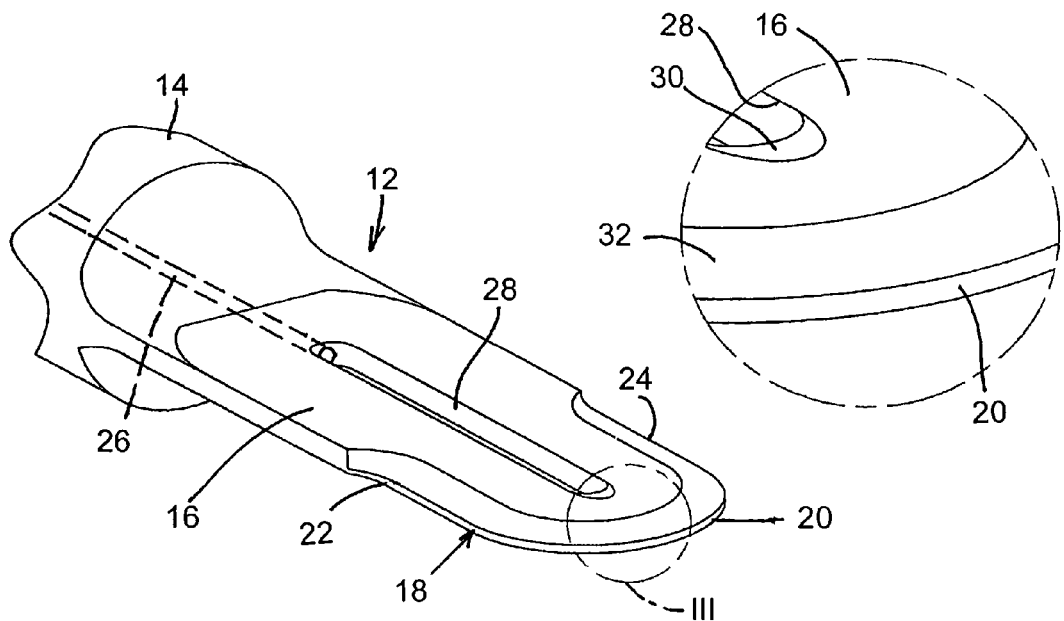
FIGURE 3
FIGURE 2

METHOD FOR ULTRASONIC TISSUE EXCISION WITH TISSUE SELECTIVITY

BACKGROUND OF THE INVENTION

This invention relates to a surgical method. More particularly, this invention relates to a method for selectively excising tissue during a surgical procedure. This invention also pertains to an ultrasonic surgical blade utilizable in performing the method.

Over the past 30 years, several ultrasonic tools have been invented which can be used to ablate or cut tissue in surgery. Wuchinich et al. in U.S. Pat. No. 4,223,676 and Idemoto et al in U.S. Pat. No. 5,188,102 disclose such devices.

Ultrasonic surgical devices generally fall into two categories. One is a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as microstreaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

A second kind of ultrasonic device uses a sharp blade instead of a blunt hollow probe. Here a cutting action takes place. Such a sharp ultrasonic blade is the subject of allowed U.S. patent application Ser. No. 440,349 filed Nov. 15, 1999, now U.S. Pat. No. 6,379,371. As disclosed therein, the blade shape is semicircular at the distal portion with two straight sides parallel to the longitudinal axis and extending back to the shoulder that contacts the vibrating probe. Male threads are shown which mate with the female threaded socket of the probe (or transducer) to allow tight intimate contact of the probe and blade tip shoulder. When the two are torqued together, they form a single resonant body that will vibrate in sympathy with the transducer and generator combination. The distal end of the blade will vibrate with an amplitude set by the mechanical gain of the probe/tip geometry and the input amplitude provided by the transducer generator combination. This motion provided the cutting action for the tissue in question.

The blade of allowed U.S. patent application Ser. No. 440,349 filed Nov. 15, 1999, now U.S. Pat. No. 6,379,371, was intended for the cutting or excising of bone or similarly hard tissue in surgical applications. In tests conducted in vitro and in vivo, it was noted that the blade, when sharp, cut both hard and soft tissue with similar ease. In delicate operations, such as sinus lift surgery or craniotomies where the goal is to cut an aperture in the front of the skull to expose sinus tissue or brain but not cut the membrane directly beneath the bony structure, this is very important. It is also important in spinal and brain surgery where bone tissue must be cut with a minimum of damage to underlying soft tissues such as the dura mater. It was noted in early in vitro testing that the blade, as it plunged through the cortex of the bone punctured the membrane or ripped it. After some experience, competent surgeons were able to master the technique, but the learning curve was steep.

A sharp blade such as that of allowed U.S. patent application Ser. No. 440,349 filed Nov. 15, 1999, now U.S. Pat. No. 6,379,371, has been shown in both in vitro and in vivo testing to be an effective tool for cutting bone, cartilage, soft tissues such as vein, arteries and can even be used to cut skin with minimal secondary trauma. In this kind of blade, ablation is not the primary cause but a shearing or cutting action predominates.

Both the ablating instrument and the cutting or incising instrument have limitations when used as surgical tools. The blunt probe is effective in ablating or excising soft liquid rich tissues such as fat, liver or spleen, but less effective or even non-effective in dry, hard material such as hard cartilage or bone. The blade type devices are effective in the hard material but also are not soft tissue sparing so that collateral tissue damage is incurred, rendering the blade undesirable around nerve clusters or other important structures. Because sharp blades tend to cut everything, tissue selectivity is reduced to nil and no differentiation may be made between hard and soft material.

In certain applications, such as sinus cavity lifts and maxialfacial surgery such as third molar extraction, a tool would be useful which could cut the harder bony material with less trauma while sparing the soft tissues underneath if they were inadvertently touched by the vibrating blade.

OBJECTS OF THE INVENTION

It is an object of the present invention to provide a surgical tool for selectively excising tissues.

More particularly, it is an object of the present invention to provide an ultrasonic cutting blade capable of selectively excising tissues.

It is an even more particular object of the present invention to provide such a blade that could be used to cut harder bony material while minimizing trauma to adjacent soft tissues in the event that those soft tissues are inadvertently touched by the vibrating blade.

A related object of the present invention is to provide a surgical method that selectively excises tissue.

A more specific object of the present invention is to provide a surgical method for cutting harder bony material while minimizing trauma to adjacent soft tissues.

These and other objects of the invention will be apparent to those skilled in the art from the drawings and descriptions hereof. Although each object is attained by at least one embodiment of the invention, no embodiment need necessarily meet every object.

SUMMARY OF THE INVENTION

The present invention is directed to a surgical blade and additionally to a method of use of that surgical blade in an ultrasonically assisted procedure. The surgical blade has a certain range of a critical dimension that permits it to be used in the method.

The invention was made only upon the observation that the sharper the blade, i.e., the smaller the minor dimension of a vertical trapezoid formed by the included angle of a blade of width N (see FIG. 1), the more likely that cutting of hard tissues resulted in collateral damage, particularly incisions, in surrounding soft tissue. The minor dimension or thickness of the blade at the edge can range from the width of the body of the blade, N, to 0. The degree of sharpness is inversely proportional to the edge thickness.

Dimensionally, it was discovered that blades with an edge thickness between approximately 0.001" and approximately 0.010" inch offered the best compromise between effective, safe cutting of hard tissue such as bone while being sparing of surrounding soft tissue.

As an added benefit, it was serendipitously noted that the blades with a less sharp configuration held their edge longer, i.e., sustained less damage than the sharper blades. It should be noted that the blades did not incur as much damage to the blade surface as the sharper blades, not that the blades started out not sharp and got worse as they were used.

Accordingly, an ultrasonic surgical blade in accordance with the present invention comprises a generally flat blade having a thickness along a cutting edge of between about 0.0005 inch and about 0.020 inch. More preferably, the cutting edge has a thickness of between about 0.001 inch and 0.010 inch. Most preferably, the cutting edge has a thickness of between about 0.001 inch and 0.003 inch. Generally, the blade has a flat body portion with a body thickness greater than the edge thickness. The blade then includes a beveled or tapered region extending from the body portion to the edge.

Pursuant to special features of the invention, the cutting edge is disposed in a single plane and has an arcuate section and a pair of straight sections continuous with the arcuate section at opposite ends thereof. Also, the blade is provided with a shank having an axially extending bore for the conveyance of cooling fluid to the cutting edge, the blade body being provided with an axially extending through-slot communicating at one end with the bore.

A surgical method in accordance with the present invention utilizes a cutting blade having a thickness along a cutting edge of preferably between about 0.0005 inch and about 0.020 inch and more preferably between approximately 0.001 inch and approximately 0.010 inch and most preferably between about 0.001 inch and 0.003 inch. During the performance of the surgical method, the blade is moved in contact with relatively hard tissue that is disposed adjacent to relatively soft tissue at a surgical site in a patient. The cutting edge may be moved at any angle relative to a surface of the hard tissue, from 90° (perpendicular) to 0° (parallel). In the latter case, the blade may move generally along an interface between the relatively hard tissue and the relatively soft tissue. The blade is ultrasonically vibrated during the moving of the blade, whereby the hard tissue is cut and, in the case of an interface incision, separated from the soft tissue, with a modicum of damage being inflicted on the soft tissue.

Pursuant to another feature of the present invention, the vibrating of the blade is initiated prior to a contacting of the surgical site with the blade and is maintained during an initial contact of the blade with the tissues at the surgical site and during the moving of the blade. The blade is moved in a continuous and uninterrupted stroke, for instance, along an interface, the ultrasonic vibrating of the blade being performed continuously and uninterruptedly during the stroke. At the end of the cutting stroke, the ultrasonic vibrating of the blade is terminated and the blade is removed from the surgical site. Irrigation fluid may be introduced to the surgical site during the moving of the blade along the interface.

BRIEF DESCRIPTION OF THE DRAWINGS

FIG. 1 is a schematic cross-sectional view, on an enlarged scale, of an ultrasonic surgical blade in accordance with the present invention.

FIG. 2 is a perspective view, also on an enlarged scale, of an ultrasonic surgical blade in accordance with the present invention.

FIG. 3 is a perspective view, on a larger scale, of a portion of the blade encircled by line III in FIG. 2.

DETAILED DESCRIPTION OF THE PREFERRED EMBODIMENTS

As illustrated in the drawings, a cutting blade 12 for use in ultrasonically assisted surgery includes an integral shank portion 14 having an external screw thread (not shown) for replaceably mounting the blade to a probe. Alternatively, blade 12 may be permanently attached to the probe.

Blade 12 includes a planar blade body 16 having a thickness N. Blade body 16 is provided at an end opposite shank 14 with a blade or cutting edge 18 including a central circularly arcuate section 20 and a pair of linear end sections 22 and 24. Edge 18 is continuous along a full radius of arcuate section 20, as well as along straight sections 22 and 24.

As further illustrated in the drawings, blade 12 also incorporates structure providing a path for coolant from an irrigation pump (not shown) to reach blade edge 18, as well as tissues being cut during a surgical procedure. For conducting irrigant to blade edge 18 and the surgical site, shank portion 14 is formed with an axial passageway or bore 26, which communicates with an axial passageway or bore in the probe.

Passageway or bore 26 terminates in an open longitudinal channel or slot 28 that enables the coolant to spread out and onto the planar body 16 of blade 12. This open channel or slot 28 distributes irrigant all along the sides or lateral surfaces of planar blade body 16 and not in only specific locations, as discussed in allowed U.S. patent application Ser. No. 440,349 filed Nov. 15, 1999, now U.S. Pat. No. 6,379,371, the disclosure of which is hereby incorporated by reference. At an end of channel or slot 28 opposite passageway or bore 26 is disposed a pair of opposed inclined surfaces 30 (only one shown) which distribute irrigant from the channel or slot towards arcuate blade edge section 20. The fluid traveling down channel or slot 28 will encounter inclined surfaces 30 which exhibit an incident angle that deflects the fluid into the cut (FIG. 10) while minimizing splash back. Surfaces 30 may be planar, convex or concave.

Blade 12 has a thickness E along cutting edge 18 of between about 0.0005 inch and about 0.020 inch, more preferably between about 0.001 inch and 0.010 inch, and most preferably between about 0.001 inch and 0.003 inch. Beveled or tapered surfaces 32 extend from the body portion 16 to edge 18. Cutting edge 18, including sections 20, 22 and 24, is disposed, as is the entire blade body 16, in a single plane.

The use of blade 12 in a surgical procedure is described in detail hereinafter. The procedure described herein is a modification of the procedure described in allowed U.S. patent application Ser. No. 440,349 filed Nov. 15, 1999, now U.S. Pat. No. 6,379,371.

In use, blade 12 was found to perform best when the following method was employed.

After the patient is prepped for surgery as per standard practices, the ultrasound unit is set up as indicated in allowed U.S. patent application Ser. No. 440,349 filed Nov. 15, 1999, now U.S. Pat. No. 6,379,371. Upon an activation of the ultrasound unit, blade 12 begins to vibrate and irrigation fluid is introduced simultaneously. Blade edge 18 is then brought into contact with hard tissue at a preselected surgical site. The vibrating blade 12 is moved in a continuous stroke over the incision site to cut or remove tissue to a desired depth. After termination of the stroke, the power to the ultrasound unit is shut off and blade 12 is removed from the surgical site.

The technique discussed above prevents tissue temperature rise to levels that would cause necrosis. If blade 12 is not moved across the surgical site in a wiping or swiping fashion, tissue temperatures quickly increase to over 49 degrees C., which in the human body is at or above the necrosis temperature. By constantly moving the blade, the temperatures rise very little over that of normal body temperatures. Also, this technique provides very good tactile feedback to allow the surgeon to discriminate between the harder tissue and the softer, viable structures.

If surgeon desires and there is enough access, he or she may move blade 12 so that it cuts along an interface between harder and softer tissues, thereby stripping the harder top layer off the soft tissue underneath. Blade 12 has good selectivity between the two layers, so that collateral damage to the soft tissue is minimized.

Preferably, a mixture of saline, lidocaine (or equivalent) and epinephrine (or equivalent) is used as the irrigant. Such a mixture provides moisturization, a slight hemostasis due to the vasocontricting action of the epinephrine, and pain relief from the action of the lidocaine. All of these chemicals have been found to be safe when used for the stated purpose in clinical practice.

Although the invention has been described in terms of particular embodiments and applications, one of ordinary skill in the art, in light of this teaching, can generate additional embodiments and modifications without departing from the spirit of or exceeding the scope of the claimed invention. For example, although the described surgical method has proven efficacious and safe in adult and pediatric maxialfacial surgery, reconstructive plastic surgery of the face and in various dental procedures, many other surgical procedures may benefit from this invention. Such other surgical procedures include brain and spinal cord surgery where bone tissue must be displaced to afford access to the tissues of the central nervous system. The present invention facilitates such surgery in that the relatively hard bone tissue may be cut with a modicum of damage inflicted on the underlying relatively soft nerve tissues and dura mater. Thus, the present invention is of use in surgery where an incision is to be made perpendicularly to an outer tissue surface or parallel to an exterior surface, e.g., along a hard-tissue/soft-tissue interface.

Accordingly, it is to be understood that the drawings and descriptions herein are proffered by way of example to facilitate comprehension of the invention and should not be construed to limit the scope thereof.

What is claimed is:

1. A surgical method comprising:
providing a cutting blade having a thickness along a cutting edge of between about 0.0005 inch and about 0.020 inch;
moving said blade in contact with relatively hard tissue located adjacent to relatively soft tissue at a surgical site in a patient, so that said cutting edge cuts through said hard tissue and leaves said soft tissue substantially intact and undamaged; and
ultrasonically vibrating said blade during the moving of said blade,
wherein the vibrating of said blade is initiated prior to a contacting of said surgical site with said blade and is maintained during an initial contact of said blade with the tissues at said surgical site and during the moving of said blade through said hard tissue,
wherein said blade is moved in a continuous and uninterrupted stroke along an interface between said hard tissue and said soft tissue at said surgical site with said blade extending generally parallel to said interface, the ultrasonic vibrating of said blade being performed continuously and uninterruptedly during said stroke.

2. The method defined in claim 1, further comprising terminating the ultrasonic vibrating of said blade and removing said blade from the surgical site upon the completion of said stroke.

3. The method defined in claim 1, further comprising introducing irrigation fluid to said surgical site during the moving of said blade along said interface.

4. The method defined in claim 1, further comprising terminating the ultrasonic vibrating of said blade and removing said blade from the surgical site after the moving of said blade along said interface.

5. The method defined in claim 1, further comprising introducing irrigation fluid to said surgical site during the moving of said blade.

6. The method defined in claim 1 wherein the thickness of said cutting edge is between about 0.001 inch and about 0.010 inch.

7. A surgical method comprising:
providing a cutting blade having a thickness along a cutting edge of between about 0.001 inch and about 0.010 inch;
moving said blade in a surgical site in a patient so that said cutting edge moves generally along an interface between relatively hard tissue and relatively soft tissue, with said cutting edge extending generally parallel to said interface; and
ultrasonically vibrating said blade during the moving of said blade along said interface, whereby said hard tissue is cut and separated from said soft tissue with a modicum of damage being inflicted on said soft tissue.

8. The method defined in claim 7 wherein the vibrating of said blade is initiated prior to a contacting of said hard tissue and said soft tissue with said blade and is maintained during an initial contact of said blade with the tissues at said surgical site and during the moving of said blade along said interface.

9. The method defined in claim 7, further comprising terminating the ultrasonic vibrating of said blade and removing said blade from the surgical site upon a completion of the moving of said blade in said surgical site.

10. The method defined in claim 7, further comprising introducing irrigation fluid to said surgical site during the moving of said blade along said interface.

* * * * *